(12) United States Patent
Marshall

(10) Patent No.: US 11,820,033 B2
(45) Date of Patent: Nov. 21, 2023

(54) KNIFE

(71) Applicant: The Safety Knife Company Limited, Quedgeley (GB)

(72) Inventor: Peter Marshall, Quedgeley (GB)

(73) Assignee: The Safety Knife Company Limited

( * ) Notice: Subject to any disclaimer, the term of this patent is extended or adjusted under 35 U.S.C. 154(b) by 69 days.

(21) Appl. No.: 16/447,579

(22) Filed: Jun. 20, 2019

(65) Prior Publication Data

US 2020/0001485 A1    Jan. 2, 2020

(30) Foreign Application Priority Data

Jun. 27, 2018   (GB) ...................................... 1810559

(51) Int. Cl.
*B26B 5/00* (2006.01)
*B26B 27/00* (2006.01)
*B26B 29/02* (2006.01)
*A61B 17/3211* (2006.01)
(Continued)

(52) U.S. Cl.
CPC ............... *B26B 5/00* (2013.01); *B26B 27/00* (2013.01); *B26B 29/02* (2013.01); *A61B 17/3211* (2013.01); *A61B 17/3213* (2013.01); *A61B 2017/32113* (2013.01); *B26B 1/10* (2013.01); *B26B 5/001* (2013.01)

(58) Field of Classification Search
CPC ............ A61B 17/3211; A61B 17/3213; A61B 2017/32113; B26B 1/10; B26B 5/00; B26B 5/001; B26B 1/08; B26B 27/00; B26B 29/02; B26B 3/00

USPC ... 30/278, 279.2, 279.6, 280, 282, 285, 286, 30/289, 294, 295, 314
See application file for complete search history.

(56) References Cited

U.S. PATENT DOCUMENTS

| | | | | |
|---|---|---|---|---|
| 397,949 | A | * | 2/1889 | Walb ........................ B26B 5/00 30/157 |
| 530,788 | A | * | 12/1894 | Moritz et al. ............. B26B 5/00 30/157 |

(Continued)

FOREIGN PATENT DOCUMENTS

| | | | | |
|---|---|---|---|---|
| DE | 1 144 437 | * | 2/1963 | ......... A61B 17/3213 |
| FR | 330571 | * | 8/1903 | ......... A61B 17/3213 |

(Continued)

OTHER PUBLICATIONS

Intellectual Property Office, Patents Act 1977: Search Report under Section 17, dated Dec. 19, 2018, p. 1, UK.

*Primary Examiner* — Jason Daniel Prone
(74) *Attorney, Agent, or Firm* — Anthony J. Bourget

(57) ABSTRACT

A knife having a first body part and a second body part cooperating with one another to allow a blade to be secured thereto, the body parts cooperate with one another such that sliding movement of the first body part relative to the second body part can occur, and a latch arrangement whereby the body parts can be latched against relative sliding movement from a first position towards a second position, the latch arrangement having a resilient member carried by the first body part and cooperable with the second body part to latch the body parts against sliding movement towards the second position, and an opening provided in the second body part through which a tool can be inserted to depress the resilient member and allow such sliding movement to occur.

19 Claims, 4 Drawing Sheets

(51) Int. Cl.
*B26B 1/10* (2006.01)
*A61B 17/3213* (2006.01)

(56) References Cited

U.S. PATENT DOCUMENTS

| | | | | |
|---|---|---|---|---|
| 1,134,407 | A * | 4/1915 | Page | B26B 1/10 30/164 |
| 1,186,480 | A * | 6/1916 | Jones | B23B 13/125 279/44 |
| 2,599,439 | A * | 6/1952 | Drake | B26B 5/006 30/294 |
| 2,802,265 | A * | 8/1957 | Ogden | A61B 17/3213 30/339 |
| 3,751,806 | A * | 8/1973 | Patrick | B26B 27/00 30/294 |
| 3,893,238 | A * | 7/1975 | Scholl | B26B 5/005 30/294 |
| 4,408,394 | A | 10/1983 | Phelps | |
| 4,646,440 | A * | 3/1987 | Decker | B26B 5/00 30/335 |
| 5,022,156 | A * | 6/1991 | Kallens | B26B 5/00 30/337 |
| 5,046,253 | A * | 9/1991 | Ireland | B26B 5/00 30/294 |
| 5,285,577 | A * | 2/1994 | Carney | B26B 27/00 30/294 |
| 5,341,822 | A * | 8/1994 | Farr | B26B 5/00 30/294 |
| 5,768,787 | A * | 6/1998 | Ireland | B26B 27/00 30/294 |
| 6,416,524 | B1 * | 7/2002 | Critz et al. | A61B 17/3213 30/315 |
| D590,687 | S * | 4/2009 | Ireland | B26B 5/00 D8/98 |
| 7,527,635 | B2 * | 5/2009 | Saito et al. | A61B 17/3213 606/167 |
| 7,857,824 | B2 * | 12/2010 | Kiehne | A61B 17/3213 606/167 |
| D655,995 | S * | 3/2012 | Ireland | B26B 1/08 D8/98 |
| D655,996 | S * | 3/2012 | Ireland | B26B 5/001 D8/98 |
| 9,102,068 | B2 * | 8/2015 | Gringer | B26B 5/001 |
| 9,862,106 | B2 * | 1/2018 | Onion | B26B 5/00 |
| 9,872,701 | B2 * | 1/2018 | Werner | A61B 17/3211 |
| 10,442,093 | B2 * | 10/2019 | Jacobs et al. | B26B 9/00 |
| 2008/0250650 | A1 * | 10/2008 | Seber | B26B 5/001 30/162 |

FOREIGN PATENT DOCUMENTS

| | | | | |
|---|---|---|---|---|
| FR | 409996 | * | 5/1910 | A61B 17/3213 |
| GB | 235500 | * | 6/1925 | A61B 17/3213 |
| GB | 225888 | * | 7/1925 | A61B 17/3213 |
| GB | 369388 | | 12/1931 | |
| GB | 2575073 A | * | 1/2020 | B26B 5/00 |

* cited by examiner

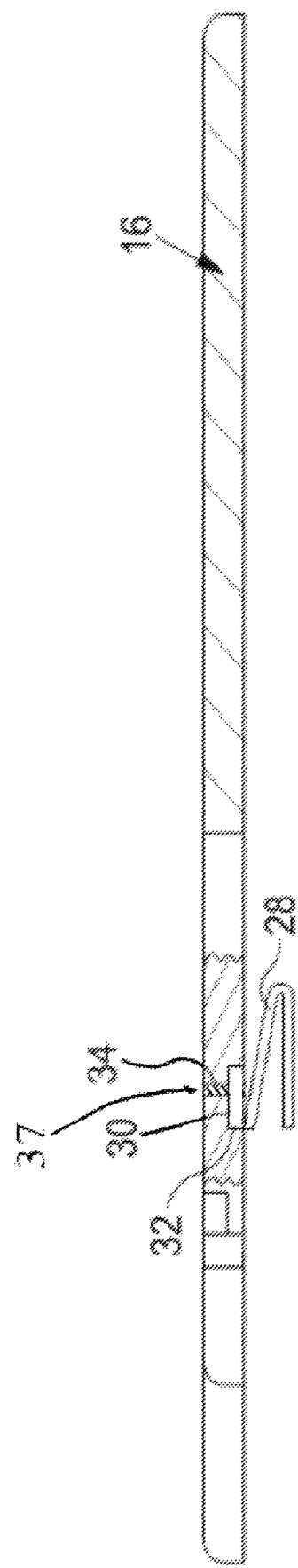

KNIFE

This invention relates to a knife, and in particular to a knife of the type in which a blade thereof can be replaced. The invention is especially applicable to safety knives of the type in which access to the cutting edge of an exposed blade is restricted so as to reduce the risk of injury to a user, but the invention is not restricted to such use and may be applied to knives of the type having exposed blades or exposed blade cutting edges.

A number of designs of a safety knife are known in which access to the cutting edge of the blade is restricted. By restricting access in this manner, the risk of a user cutting himself, for example, is reduced. Access to the cutting edge of the blade may be restricted using guards which restrict the exposed length of the cutting edge, and which restrict the size of objects able to reach the cutting edge to a size smaller than, for example, a typical adult human finger so that the user is unlikely to be able to cut himself during normal use. Another type of safety knife uses side guards positioned parallel to but spaced slightly from the face of the blade to restrict access thereto, the sideguards being retracted when cutting is to take place.

In many designs, the body of the knife is of a suitable plastics material, the blade being moulded into the body. After a period of use, the blade becomes dulled or blunt and at that point the knife is disposed of. Clearly, as it is only the blade of the knife that has become worn in such circumstances, disposing of the entire knife is wasteful. It would be desirable for the knife to be designed in such a manner as to allow replacement of the blades.

Some knife designs include a body of two part or multi-part form which can be opened to allow blade replacement to take place. Whilst knives of this type may be advantageous in that disposal of a knife body simply because a blade has become worn is avoided, allowing a user to open the knife body to replace the blade results in the user being exposed to unprotected blade cutting edges during the blade replacement process. Whilst in normal use, therefore, the user may be protected, byt during blade change operations the user may be exposed to an unacceptably high risk of injury.

It is an object of the invention, therefore, to provide a knife in which changing of blades is possible, but in which the likelihood of injury occurring during a blade replacement operation is reduced.

According to the present invention there is provided a knife comprising a knife body of at least two part form, the knife body comprising a first body part and a second body part, the first and second body parts cooperating with one another to allow a blade to be secured thereto, the first and second body parts including interengaging formations which cooperate with one another such that sliding movement of the first body part relative to the second body part can occur, the formations securing the body parts to one another in a first relative position of the body parts, and allowing separation of the body parts in a second relative position thereof, and a latch arrangement whereby the first and second body parts can be latched against relative sliding movement from the first position towards the second position, the latch arrangement comprising a resilient member carried by the first body part and cooperable with the second body part to latch the body parts against sliding movement towards the second position, and an opening provided in the second body part through which a tool can be inserted to depress the resilient member and allow such sliding movement to occur.

It will be appreciated that such an arrangement is advantageous in that opening of the knife body is restricted to those with the required tool. Accordingly, opening of the knife body to allow blade replacement to be undertaken may be restricted to those suitably trained and skilled to ensure that the risk of injury is maintained at an acceptably low level.

The interengaging formations of one of the body parts may take the form of projections, the interengaging formations of the other of the body parts taking the form of, for example, key-hole slots able to cooperate with the projections to releasably secure the body parts to one another. However, other shaped formations are possible. By way of example, one of the body parts may include projections each of which includes an overhang in the direction of relative sliding movement, the other of the body parts defining openings through or into which the projections can extend and ledges defining pockets receiving the overhangs when in the first position to secure the body parts to one another.

The knife may take a range of forms. It could comprise, for example a scalpel or craft knife, or another form of knife with a blade that is exposed, in use. However, the invention is particularly beneficial when applied to knives of the type in which the cutting edge of the blade is guarded, by guarding structure in use. By way of example, the knife body may be shaped to define a narrow recess across which the blade extends, the recess being sufficiently small that access to the cutting edge of the blade is restricted. Alternatively, the blade may be of hooked form, shaped to restrict access to the cutting edge thereof. Another possibility is that the knife body carries a guard member which extends alongside the blade, providing protection against accidental cutting. It will be appreciated that these represent examples of the types of knife with which the invention may be employed, and that the invention is not restricted to these examples.

The knife may carry a sticker or label covering the opening and so disguising the manner in which opening of the knife body is achieved. If desired, the opening may be filled with a suitable filler, for example in the form of an adhesive, reducing the risk of the knife body being opened.

As the knife body is designed to be reused, it may be preferred to form it from, for example, a metallic material rather than a plastics material.

The invention will further be described, by way of example, with reference to the accompanying drawings, in which.

Figure 2:
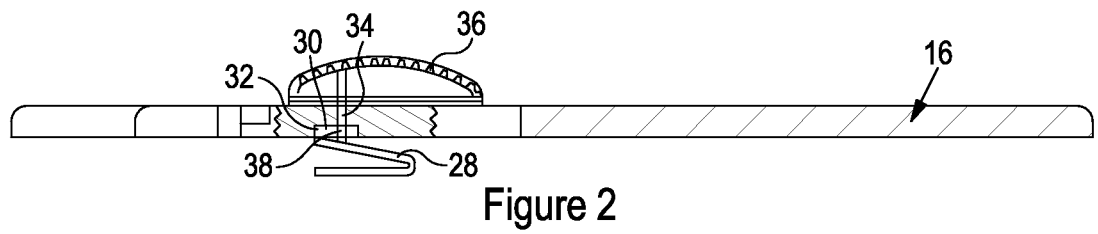
FIG. 2 is a cross-sectional view illustrating part of the knife of FIG. 1.
Figure 4:
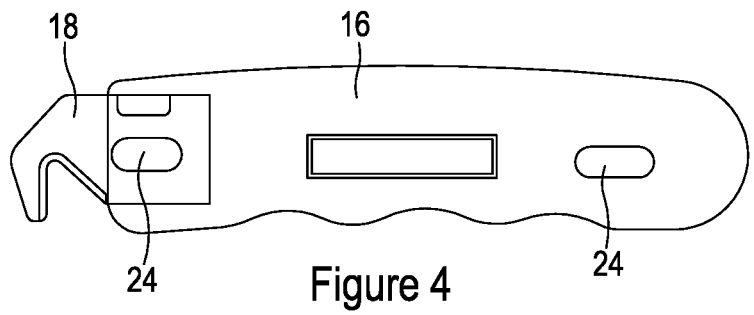
FIGS. 4 and 5 are views illustrating parts of a knife according to another embodiment of the invention.
Figure 5:
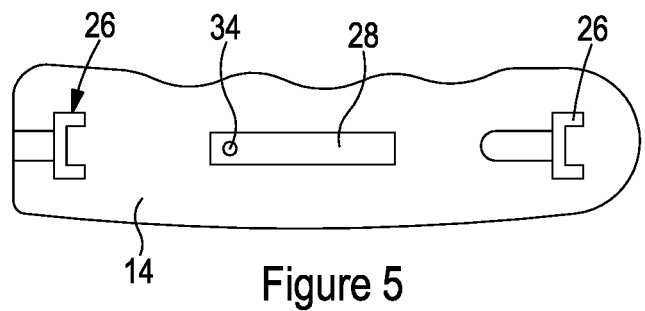
Figure 6:
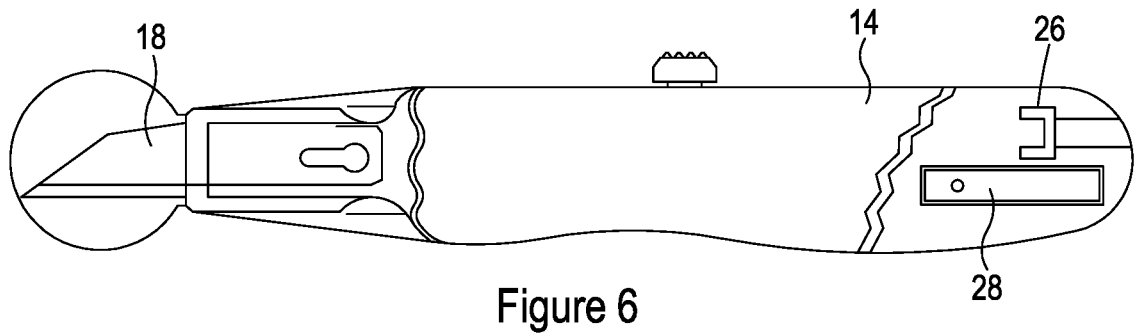
Figure 7:
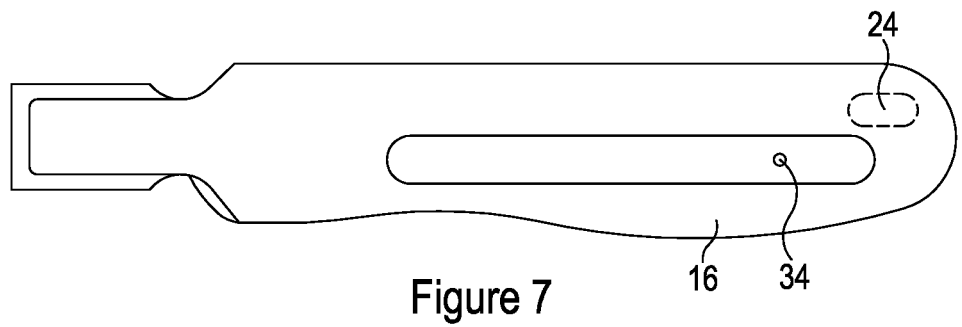
Figure 8:
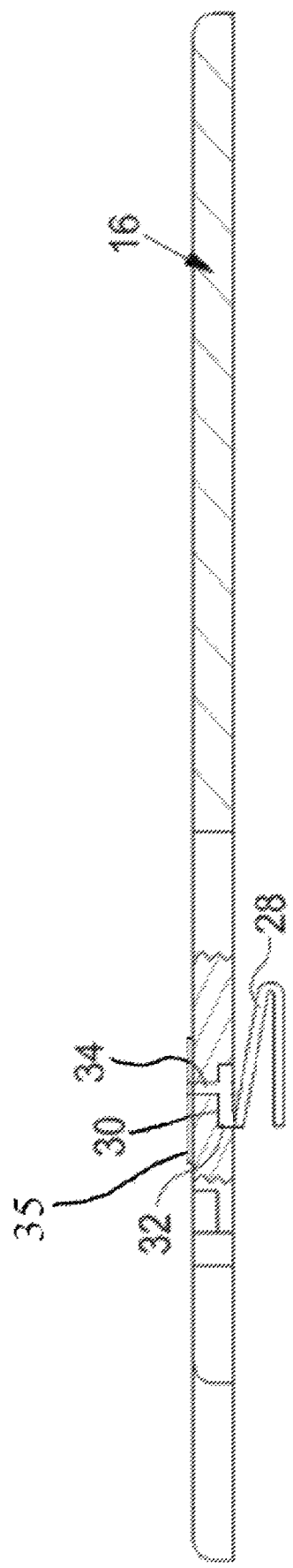

FIGS. 6 and 7 are views similar to FIGS. 4 and 5 illustrating a further embodiment of the invention; and FIGS. 8 and 9 are views similar to FIG. 2 illustrating further aspects of the invention.

Figure 1:
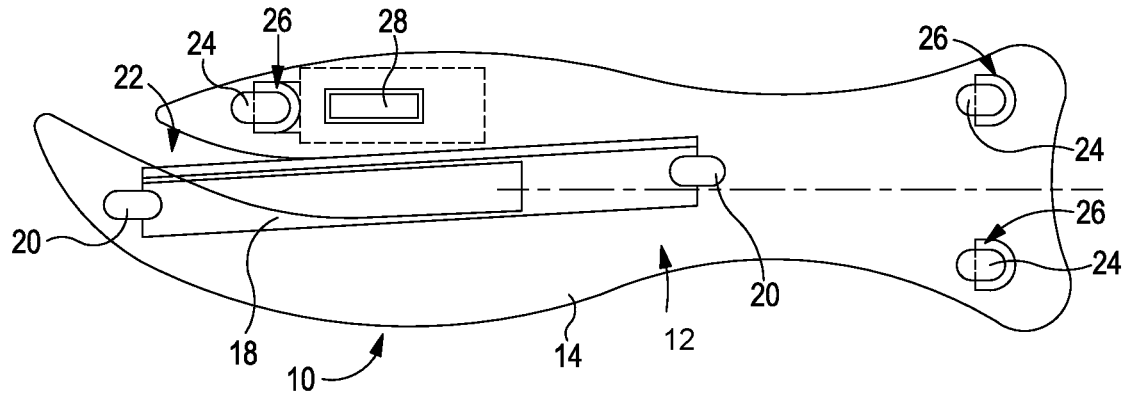
FIG. 1 is a view illustrating a knife in accordance with an embodiment of the invention.
Figure 3:
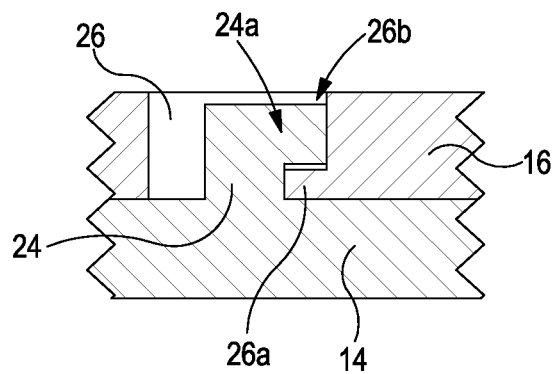
FIG. 3 is a view illustrating a manner in which parts of the knife body of the knife of FIG. 1 are secured to one another.

Referring firstly to FIGS. 1 to 3, a safety knife 10 is illustrated. The knife 10 comprises a knife body 12 of two part form, comprising a first body part 14 and a second body part 16. The body parts 14, 16, when fitted to one another, define a void within which a blade 18 is located, retaining features 20 being moulded into the body parts 14, 16 to firmly retain the blade 18 in position. The knife body 12 is shaped to define a recess 22 of width smaller than the width of a typical adult human finger, the blade 18 being positioned such that it extends across the recess 22.

In use, material to be cut using the knife 10 is fed into the recess 22, usually by movement of the knife 10 across the material to be cut. The material being fed into the recess 22 comes into engagement with the cutting edge of the blade 18 and is cut by the blade 18. As access to the cutting edge of the blade 18 is restricted, the only exposed part of the cutting edge being located within the recess 22, only materials of small dimensions are able to reach the cutting edge. In particular, a user's fingers, for example, are unable to access the cutting edge. Accordingly, the risk of injury to the user is reduced.

As the knife is designed in such a manner that the risk of injury is reduced, it is suitable for use in workplaces of the type in which the employer has a duty to minimise risks to which employees may be exposed.

As mentioned above, the knife body 12 is of two part form, comprising the first body part 14 and the second body part 16. The body parts are secured to one another by interengaging formations designed to allow the body parts to slide relative to one another between a first, in use, assembled position, in which the body parts are aligned with one another, and a second, disassembly position. As shown in FIG. 1, the first body part 14 is provided with a series of upstanding projections 24. In the arrangement shown, three such projections 24 are provided, but it will be appreciated that more or fewer projections may be provided if required, and that the positions of the projections may be modified to suit the design. As best shown in FIG. 3, each projection 24 includes an enlarged head 24a defining an overhang. The second body part 16 is provided with openings 26 positioned to align with the projections 24. Each opening 26 is of dimensions chosen to allow the enlarged head 24a to pass into the respective opening 26. Each opening 26 is further shaped to define a ledge 26a that is of dimensions allowing it to be received, at least in part, beneath the head 24a, the ledge 26a defining a pocket 26b receiving part of the enlarged head 24a. The positions of the projections 24 and openings 26 are such that when the body parts 14, 16 are aligned within one another, the ledge 26a is received beneath the enlarged head 24a.

In use, to assemble the knife body 12, the first and second body parts 14, 16 are brought close to one another and the projections 24 are introduced into the openings 26. In this position, the body parts are slightly misaligned relative to one another. After introducing the projections 24 into the openings 26, the body parts 14, 16 are brought into contact with one another and are then slid relative to one another to bring the body parts 14, 16 into alignment with one another, this movement resulting in the ledges 26a being received beneath the respective enlarged heads 24a. The cooperation between the enlarged heads 24a and ledges 26a secures the body parts to one another.

As shown in FIGS. 1 and 2, a resilient latch arrangement in the form of a leaf spring 28 is located within the body, being secured to the first body part 14 and arranged such that a free end thereof abuts an internal surface of the second body part 16 when the body parts 14, 16 are secured to one another as described hereinbefore. The spring 28 has a first longitudinal portion and a second longitudinal portion forming an acute angle with respect to the first longitudinal portion (see FIG. 2). The second body part 16 is formed with an abutment 32 at least partially defining a recess 30 with an abutment 32 at least partially defining a recess 30 with which the end of the spring 28 engages, the engagement serving to resist relative sliding movement between the first and second body parts 14, 16 in the direction that would allow release of the body parts 14, 16 from one another. The latch arrangement thus serves to lock the body 12 in a closed position and so restricts access to the parts of the blade 18 located within the body 12.

To allow opening of the body 12, an opening 34 is provided in the second body part 16, the opening 34 being aligned with the recess 30. In use, a tool 36 including a projecting pin 38 is used to release the latch, the pin 38 being inserted into the opening 34 and engaging the spring 28, a load applied to the tool 36 depressing the spring 28 to move the spring 28 out of the recess 30, after which sliding movement of the body parts 14, 16 may be undertaken to open the body 12. Upon assembly of the knife body 12, the spring 28 will automatically engage within the recess 30 once the body parts 14, 16 occupy their first, aligned position, automatically latching the body parts 14, 16 against relative movement.

If desired, and as shown in FIGS. 8 and 9, the presence of the opening 34 may be disguised by positioning a sticker 35 over the opening 34 or by applying a suitable filler 37 such as an adhesive resin to the opening 34. Such stickers 35 or fillers 37 may also be beneficial in that they may prevent contaminants building up within the opening 34 and knife body 12.

In use, once a blade 18 becomes blunt, dulled or damaged, the knife may be passed to an authorised blade replacement operative who may open the body 12, using the tool 36 to release the latch arrangement. Once the body 12 has been opened, the operative can replace the blade and then reassemble the knife body 12 ready for the knife to be reused. It will be appreciated that, in this manner, disposal of the knife body simply as a result of the blade being blunt, dull or damaged is avoided. As opening the knife body 12 is restricted to those suitably trained, the risk of injury during blade replacement may be reduced or restricted.

As the knife body is designed to be reused, it may be of, for example, a metallic material rather than of a plastics material. The use of metallic materials may be beneficial in that cleaning or sterilisation thereof may be readily undertaken, and so the knives may be suitable for use in clean environments.

It is envisaged that blade replacement may be undertaken at the knife assembly plant where the operators are experienced in handling blades with exposed cutting edges, and so the risk of injury is reduced.

Whilst FIGS. 1 to 3 illustrate one form of knife in accordance with the invention, it will be appreciated that the invention is not restricted in this regard and may be applied to other designs of knife. FIGS. 4 to 7 illustrate two alternative designs embodying the invention, in each case the knife body being of two part form, the parts being adapted to be slid together in a manner similar to that described hereinbefore, and in each case a releasable latch arrangement being provided to resist separation of the body parts from one another, the latch arrangement taking substantially the form described hereinbefore. In FIGS. 4 and 5, the knife is of a type including a hook shaped blade the shape of which restricts access to the cutting edge thereof, and in FIGS. 6 and 7, the knife includes a side guard extending from one of the body parts so that the side guard is adjacent the blade for added safety. It will be appreciated that these are merely examples, and that the invention may be applied to a wide range of other knife designs, both those in which access to the cutting edge of the blade is restricted in normal use and to those in which the cutting edge is exposed in normal use.

Whilst specific embodiments of the invention are described hereinbefore and illustrated in the accompanying drawings, it will be appreciated that a wide range of modifications and alterations may be made thereto without departing from the scope of the invention as defined by the appended claims.

The invention claimed is:

1. A knife comprising a knife body of at least two part form, and a blade, the knife body comprising a first body part and a second body part, the first and second body parts cooperating with one another to secure the blade thereto, the first and second body parts including interengaging formations which cooperate with one another such that sliding movement of the first body part relative to the second body part can occur, the formations securing the body parts to one another in a first relative position of the body parts, and allowing separation of the body parts in a second relative position thereof, and a spring whereby the first and second body parts are latched against the relative sliding movement from the first position towards the second position, the spring carried by the first body part and cooperating with the second body part, to latch the body parts against the sliding movement towards the second position, and an opening provided in the second body part through which a tool, or part thereof, can be inserted to depress the spring and allow the sliding movement to occur, wherein the spring is secured to the first body part and is arranged such that an end part thereof abuts, in use, an internal surface of the second body part when the body parts are in the first relative position, and wherein the second body part includes an abutment with which the end part of the spring engages when the body parts are in the first relative position.

2. A knife according to claim 1, wherein the spring comprises a leaf spring.

3. A knife according to claim 1, wherein the interengaging formation of one of the body parts takes the form of a projection, the interengaging formation of the other of the body parts taking the form of a slot which cooperates with the projection to releasably secure the body parts to one another.

4. A knife according to claim 3, wherein the projection includes an overhang in a direction of the relative sliding movement, the slot including a ledge defining a pocket receiving the overhang when in the first position to secure the body parts to one another.

5. A knife according to claim 1, wherein the second body part carries a sticker or label covering the opening, the sticker or label being removable before the tool, or part thereof, is inserted into the opening.

6. A knife according to claim 1, wherein the opening is filled with a removable filler.

7. A knife according to claim 1, wherein the knife body is of a metallic material.

8. A knife according to claim 1, wherein the blade is exposed.

9. A knife according to claim 1, further comprising a guard extending from one of the body parts so that the guard is adjacent the blade.

10. A knife according to claim 1, wherein the interengaging formations of one of the body parts are projections and the interengaging formations of the other of the body parts are slots which respectively cooperate with the projections to realeasably secure the body parts to one another.

11. The knife of claim 1, wherein the first and second body parts are configured to define a recess so that only a portion of the blade is exposed while remaining portions of the blade are covered or guarded by the first and second body parts.

12. The knife of claim 1, wherein the second body part defines a recess, the abutment accessible via the recess.

13. A knife comprising a knife body of at least two part form, and a blade, the knife body comprising a first body part and a second body part, the first and second body parts cooperating with one another to secure the blade thereto, the first and second body parts including interengaging formations which cooperate with one another such that sliding movement of the first body part relative to the second body part can occur, the formations securing the body parts to one another in a first relative position of the body parts, and allowing separation of the body parts in a second relative position thereof, and a spring whereby the first and second body parts are latched against the relative sliding movement from the first position towards the second position, the spring carried by the first body part and cooperating with the second body part to latch the body parts against the sliding movement towards the second position, and an opening provided in the second body part through which a tool, or part thereof, can be inserted to depress the spring and allow the sliding movement to occur, wherein the spring is secured to the first body part and has a first longitudinal portion extending toward the second body part, the spring arranged such that a terminal end of the first longitudinal portion abuts, in use, an internal surface of the second body part when the body parts are in the first relative position.

14. The knife of claim 13 where the terminal end abuts the second body part within a recess defined by the second body part.

15. The knife of claim 13 where the spring includes a second longitudinal portion forming an acute angle with respect to the first longitudinal portion.

16. A knife comprising a knife body of at least two part form, and a blade, the knife body comprising a first body part and a second body part, the first and second body parts cooperating with one another to secure the blade thereto, the first and second body parts including interengaging formations which cooperate with one another such that sliding movement of the first body part relative to the second body part can occur, the formations securing the body parts to one another in a first relative position of the body parts, and allowing separation of the body parts in a second relative position thereof, and a resilient member whereby the first and second body parts are latched against the relative sliding movement from the first position towards the second position, the resilient member abuts the second body part to prevent the sliding movement towards the second position, and an opening provided in the second body part through which a tool, or part thereof, can be inserted to depress the resilient member and allow the sliding movement to occur, whereby removal of the blade from the body part is prevented until the first body part and second body part are separated.

17. The knife of claim 16 wherein the resilient member is a spring having a terminal end which abuts against an inner surface of the second body part to prevent the relative sliding movement from the first position toward the second position while the blade remains within the knife body.

18. The knife of claim 16 wherein the second body part includes an abutment with which an end part of the resilient member engages when the body parts are in the first relative position.

19. The knife of claim 16 wherein the second body part is formed with an abutment oriented generally perpendicular to a direction of the sliding movement at which abutment the resilient member engages when the body parts are in the first relative position.

* * * * *